(12) United States Patent
Grant

(10) Patent No.: US 6,672,300 B1
(45) Date of Patent: Jan. 6, 2004

(54) RESPIRATION ASSISTOR

(76) Inventor: Graham Cameron Grant, 19 Lockley Pde., East Roseville, NSW 2069 (AU)

(*) Notice: Subject to any disclaimer, the term of this patent is extended or adjusted under 35 U.S.C. 154(b) by 0 days.

(21) Appl. No.: 10/018,495

(22) PCT Filed: Jun. 23, 2000

(86) PCT No.: PCT/AU00/00713
§ 371 (c)(1),
(2), (4) Date: Feb. 28, 2002

(87) PCT Pub. No.: WO00/78380
PCT Pub. Date: Dec. 28, 2000

(30) Foreign Application Priority Data

Jun. 23, 1999 (AU) .......................................... PQ 4954

(51) Int. Cl.[7] .......................... A61M 16/00; A62B 7/04; F16K 31/26
(52) U.S. Cl. ........................... 124/204.26; 128/204.21; 128/204.22; 128/204.23; 128/205.24
(58) Field of Search ....................... 128/204.21, 204.22, 128/204.23, 204.26, 205.24

(56) References Cited

U.S. PATENT DOCUMENTS

| | | | | |
|---|---|---|---|---|
| 3,850,170 A | * | 11/1974 | Cox ....................... | 128/204.24 |
| 4,340,044 A | * | 7/1982 | Levy et al. ............. | 128/204.21 |
| 4,637,386 A | * | 1/1987 | Baum .................... | 128/204.21 |
| 4,966,141 A | * | 10/1990 | Bacaner et al. ........ | 128/207.14 |
| 5,044,362 A | * | 9/1991 | Younes ................. | 128/204.21 |
| 5,107,830 A | * | 4/1992 | Younes ................. | 128/204.18 |
| 5,503,146 A | * | 4/1996 | Froehlich et al. ...... | 128/204.23 |
| 5,572,993 A | * | 11/1996 | Kurome et al. ........ | 128/204.23 |
| 5,664,562 A | * | 9/1997 | Bourdon ................ | 128/204.23 |
| 5,694,926 A | * | 12/1997 | DeVries et al. ........ | 128/205.24 |
| 5,823,186 A | * | 10/1998 | Rossen et al. ......... | 128/204.21 |
| 5,868,133 A | * | 2/1999 | DeVries et al. ........ | 128/204.21 |
| 5,881,722 A | * | 3/1999 | DeVries et al. ........ | 128/204.21 |
| 5,931,160 A | * | 8/1999 | Gilmore et al. ........ | 128/204.21 |
| 6,095,139 A | * | 8/2000 | Psaros ................... | 128/204.22 |
| 6,131,571 A | * | 10/2000 | Lampotang et al. ... | 128/204.21 |
| 6,390,091 B1 | * | 5/2002 | Banner et al. ......... | 128/204.21 |
| 6,401,713 B1 | * | 6/2002 | Hill et al. .............. | 128/204.21 |

* cited by examiner

*Primary Examiner*—Weilun Lo
*Assistant Examiner*—Michael G. Mendoza
(74) *Attorney, Agent, or Firm*—Larson & Taylor PLC

(57) ABSTRACT

A respiration assistor (10) for use in an anaesthesia breathing system. The respiration assistor is intended to provide respiratory assistance for a patient (14) who is breathing spontaneously under anaesthesia in order that the patient's end-expired $CO_2$ will be maintained at or near the normal physiological level. For this purpose, the respiration assistor incorporates a blower (15) which is located in series with a gas flow detector (20 or 39) and an electric control circuit (19) is provided for activating the blower (15) when inspired gas flow is detected by the detector (20 or 39). Also, the respiration assistor incorporates an expiratory valve (23) that is actuated to a closed condition when the blower is activated. The respiration assistor is intended to be activated as and when required by an anaesthetist to provide in-phase respiratory assistance to a patient who is breathing spontaneously and, in any case, the respiration assistor remains in-circle with and does not affect the normal function of an associated circle absorber.

15 Claims, 3 Drawing Sheets

RESPIRATION ASSISTOR

FIELD OF THE INVENTION

This invention relates to a respiration assistor for use in a breathing system. The invention has been developed primarily for use in conjunction with anaesthesia breathing systems and the invention is herein described in that context. However, it will be understood that the invention does have broader application, for example for use in conjunction with breathing systems that are employed in intensive care and high dependency hospital environments for weaning patients off ventilators and alleviating respiratory insufficiencies.

BACKGROUND OF THE INVENTION

A typical anaesthesia breathing system, when reduced to its essential elements, comprises an inspiratory limb, an expiratory limb, a Y-piece joining the two limbs at the patient side of the system, and a T-junction joining the two limbs at the so-called bag side of the system. A reservoir bag (also known as a rebreathing bag) is connected to the T-junction and, in a semi-closed circuit system, a $CO_2$ absorber is connected in circuit with the inspiratory limb at the bag side of the system. An inspiratory valve is located in the inspiratory limb, between the $CO_2$ absorber and the Y-piece in the case of the semi-closed system, and a fresh gas inflow connection is provided between the $CO_2$ absorber and the inspiratory valve. An expiratory valve is located in the expiratory limb, between the Y-piece and the T-junction, and an adjustable pressure limiting (APL) valve is located in the expiratory limb between the expiratory valve and the T-junction for the purpose of venting excess gas from the system.

Monitoring of expired gases for $CO_2$ has been adopted widely in recent times and, as a result, it has become more evident that some patients who breathe spontaneously during anaesthesia tend to underventilate. As a consequence, the patients manifest a higher-than-desirable end-expiratory $CO_2$ level, and this has been observed particularly in older patients for whom the $SpO_2$ level may be considered satisfactory but for whom the $EtCO_2$ readings have been observed to rise to levels that indicate the need for ventilatory assistance. This assistance may be provided by squeezing the reservoir bag intermittently to produce positive pressure respiration or, if synchronised with the patient's inspiratory efforts, to provide periodic manual assistance.

However, using the reservoir bag to provide manual assistance is inconvenient for an anaesthetist. It intrudes upon other demanding activities, and creates a need to readjust the APL valve and to "chase" continually the ventilatory parameters.

The present invention is directed to an apparatus which is intended to be used to provide respiratory assistance for patients who breathe spontaneously during anaesthesia, so that the end-expired $CO_2$ level will be maintained at or near the normal physiological level.

SUMMARY OF THE INVENTION

Broadly defined, the present invention provides a respiration assistor for use in a breathing system and which comprises:

a) a gas supply passage,
b) a gas flow detector located in the gas supply passage and arranged to detect through flow of inspired gas,
c) an electrically activatable pressure booster connected in circuit with the gas supply passage, the pressure booster being of a type through which inspired gas may be drawn independently of electrical activation of the pressure booster,
d) a gas delivery conduit for delivering pressurised gas to a patient from the pressure booster,
e) an electrically actuatable expiratory valve,
f) a gas exhaust conduit for carrying expired gas from the patient to the expiratory valve,
g) means for connecting a gas supply in circuit with the gas supply passage, and
h) an electrical control circuit arranged to
   i. effect activation of the pressure booster and closure of the expiratory valve upon detection of inspired gas flow through the gas flow detector, and
   ii. effect deactivation of the pressure booster and opening of the expiratory valve in the absence of inspired gas flow through the gas flow detector.

OPERATING FEATURES OF THE INVENTION

The gas supply to which the respiration assistor is in use connected will normally comprise a circuit that includes a flow activated expiratory valve, a pressure relief (excess gas release) valve, a reservoir bag, a $CO_2$ absorber (in the case of a semi-closed system), a fresh gas inlet connection and a flow activated inspiratory valve. With this circuit connected between the electrically actuatable expiratory valve and the gas flow detector, inspiratory breathing of a patient will result in gas being drawn through the inspiratory valve and the gas flow detector. The pressure booster will then be activated and the electrically actuated expiratory valve will be closed, resulting in slight pressurisation of the patient circuit and assisted inflation of the patient's lungs. Continuing operation of the pressure booster will result in continuing suction of gas through the inspiratory valve and the gas flow detector until the lungs reach full capacity. On reaching full lung capacity, inspiration ceases, the inspiratory valve closes and normal expiration commences. When this condition is sensed by the gas flow detector, the pressure booster is deactivated and the electrically actuatable expiratory valve is opened, so that normal lung deflation and gas expiration may continue.

An important feature of the invention is that respiration assistance is provided at the patient side of the complete breathing system without interfering with system components that normally are provided at the bag side of the system. This means that a reservoir bag may be used in conjunction with the respiration assistor, this in turn meeting the needs of practising anaesthetists.

PREFERRED FEATURES OF THE INVENTION

The pressure booster preferably comprises a blower that is connected in series with the gas flow detector, and the respiratory assistor is hereinafter described as having a pressure booster in the form of a blower.

The blower is selected and energised to assist inflation of the lungs but without interfering with spontaneous respiration by the patient. The blower preferably is driven by an electric motor and the motor may be energised in one of two ways for the purpose of activating the blower. That is, the motor may be energised periodically to provide the required blower drive or the motor may be energised permanently and be connected periodically to the blower by way of an electromagnetic coupling or the like. In either case, the blower will be disconnectable from the electric motor to enable sterilisation of the gas circuit components of the respiration assistor.

The gas flow detector preferably is integrated with an inspiratory valve and, in such case, the flow activated inspiratory valve might be omitted from the gas supply circuit. Alternatively, two inspiratory valves might be connected in series, with one in the respiration assistor integrating the gas flow detector, The invention will be more fully understood from the following description of embodiments of a respiration assistor for use in an anaesthesia breathing system. The description is provided with reference to the accompanying drawings.

DETAILED DESCRIPTION OF THE INVENTION

Figure 1:
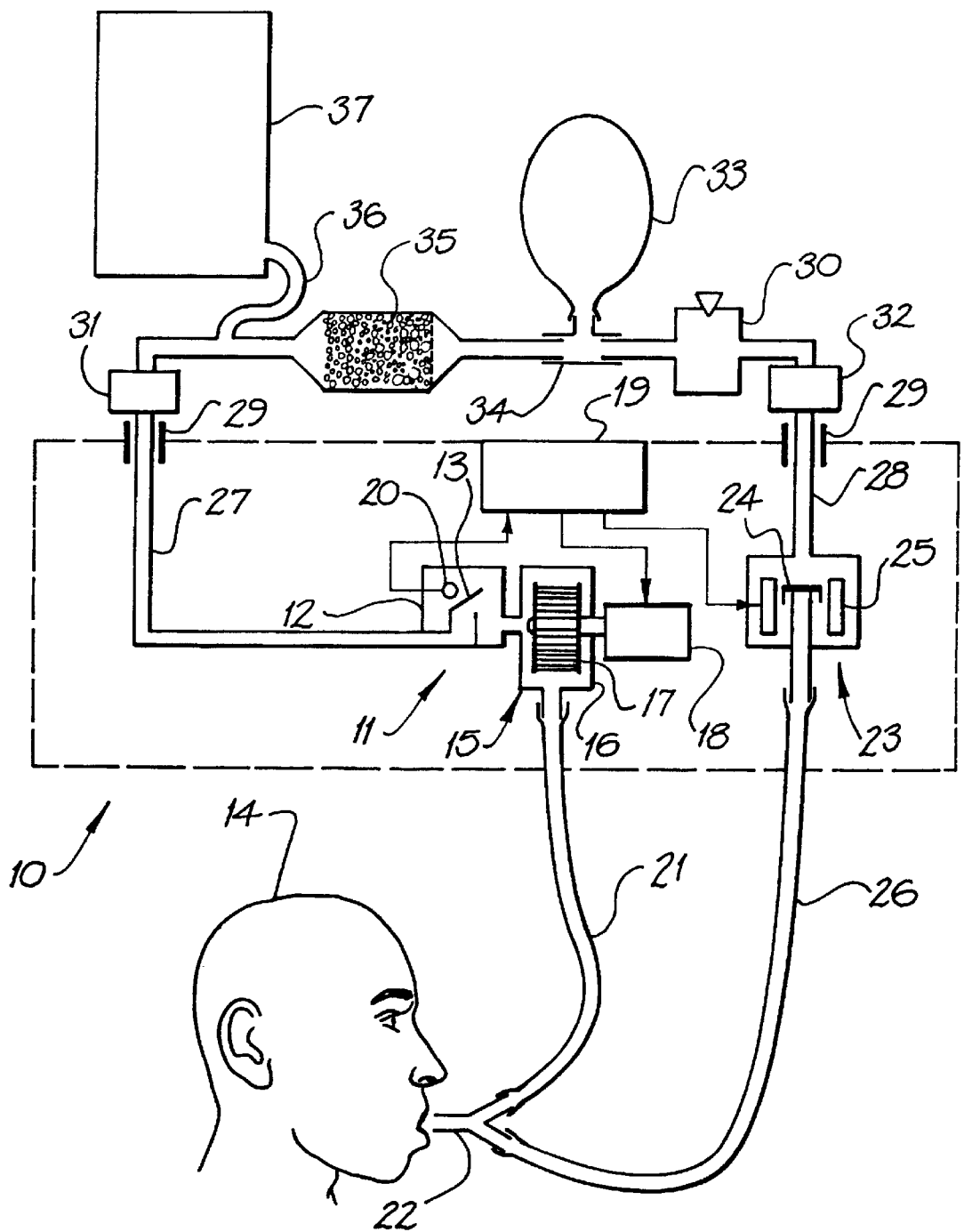
FIG. 1 provides a schematic illustration of a preferred embodiment of the respiration assistor and a connected gas conditioning-supply circuit, FIG. 2 provides a schematic illustration of an alternative embodiment of the respiration assistor and, again, a connected gas conditioning-supply circuit.

The respiration assistor 10 as illustrated in FIG. 1 comprises an inspiratory valve 11 having a valve casing 12 and a valve member 13. The valve member 13 is normally closed but is arranged to open automatically to permit gas passage with inspiratory breathing by a patient 14. The inspiratory valve 11 may be similar to the type that conventionally is used in anaesthesia breathing systems.

A centrifugal blower 15 is connected in series with the inspiratory valve 11. The blower has a casing 16 and a vaned drum-type rotor 17 through which gas may be drawn by the patient 14, with normal inspiratory breathing, prior to activation of the blower. An electric motor is removably coupled to the blower rotor 15 and is energised by way of a control circuit and power supply 19.

A sensor 20, for example a photo-electric sensor, is located within the valve casing 12 and is connected electrically with the control circuit 19. The sensor 20 functions to sense the operating state of the valve member 13 and, when the valve member is inducted to open by inspiratory breathing by the patient, a valve-open signal is employed in the control circuit 19 to generate an energising signal for the motor 18.

A flexible gas delivery conduit 21 is connected to the high pressure side of the blower 15. The delivery conduit is provided for delivering gas to the patient 14 by way of a conventional Y-piece 22.

The respiration assistor 10 also incorporates an electrically actuatable expiratory valve 23. The valve incorporates a solenoid actuated valve member 24 which normally is biased to an open condition but which is moved to a closed condition with energisation of the solenoid 25.

The solenoid 25 is energised from the control circuit 19 when opening of the inspiratory valve 11 is sensed, and the expiratory valve member 24 is maintained in a closed condition for the period during which energisation of the motor 18 is maintained.

A flexible gas exhaust conduit 26 is connected to the Y-piece 22 and is employed for carrying expired gas from the patient 14 to the expiratory valve 23.

An inlet conduit 27 is provided for delivering gas to the inspiratory valve 11, and an outlet conduit 28 is provided for conveying gas from the expiratory valve 23. Also, gas line couplings 29 are provided for connecting an existing gas conditioning/supply circuit (i.e. a standard anaesthetic circle absorber) to the respiration assistor.

The gas conditioning/supply circuit does not form a part of the respiration assistor 10 but it includes an adjustable pressure limiting (APL) valve 30 for releasing excess gas from the system and the usual flow activated inspiratory and expiratory valves 31 and 32. A reservoir bag 33 also is connected in the circuit by way of a T-junction 34 and a $CO_2$ absorber 35 is located in series with the valves. An inlet connection 36 is provided for connecting the complete system to a supply 37 of anaesthetic gas and oxygen.

Figure 2:
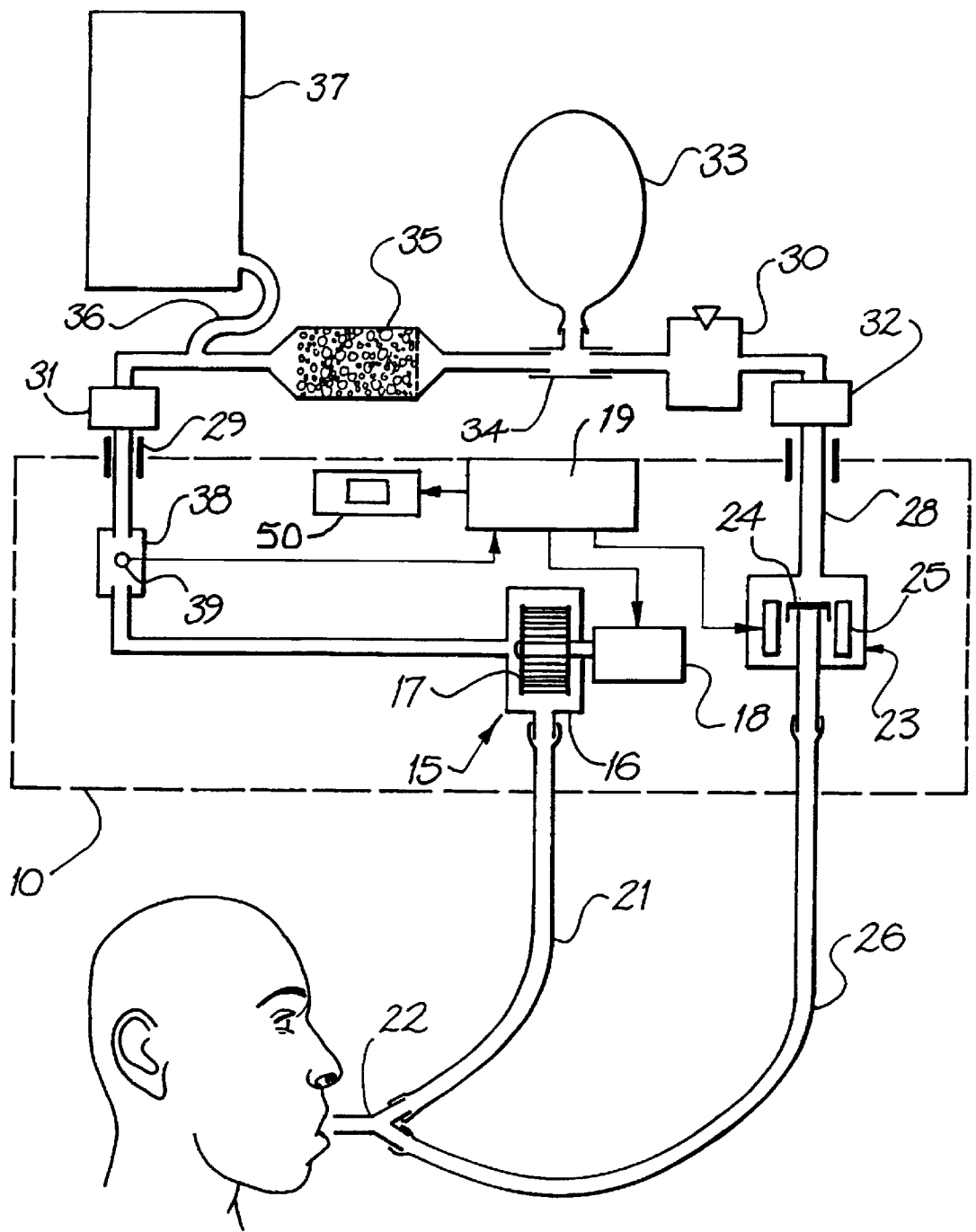

In the embodiment of the respiration assistor illustrated in FIG. 2 most of the components are similar to those shown in FIG. 1 and like reference numerals are used to identify like parts. However, the respiration assistor relies upon the provision of a single inspiratory valve, i.e. the gas supply circuit inspiratory valve 31, and inspiratory gas flow is detected by a gas flow detector 39 within a casing 38. The gas flow detector 39 may take the form of any number of known devices.

As in the case of the previously described embodiment, the output signal from the gas flow detector 39 is employed to initiate energisation of the motor 18 and actuation of the electrically actuated expiratory valve 23 by way of the control circuit 19.

Figure 3:
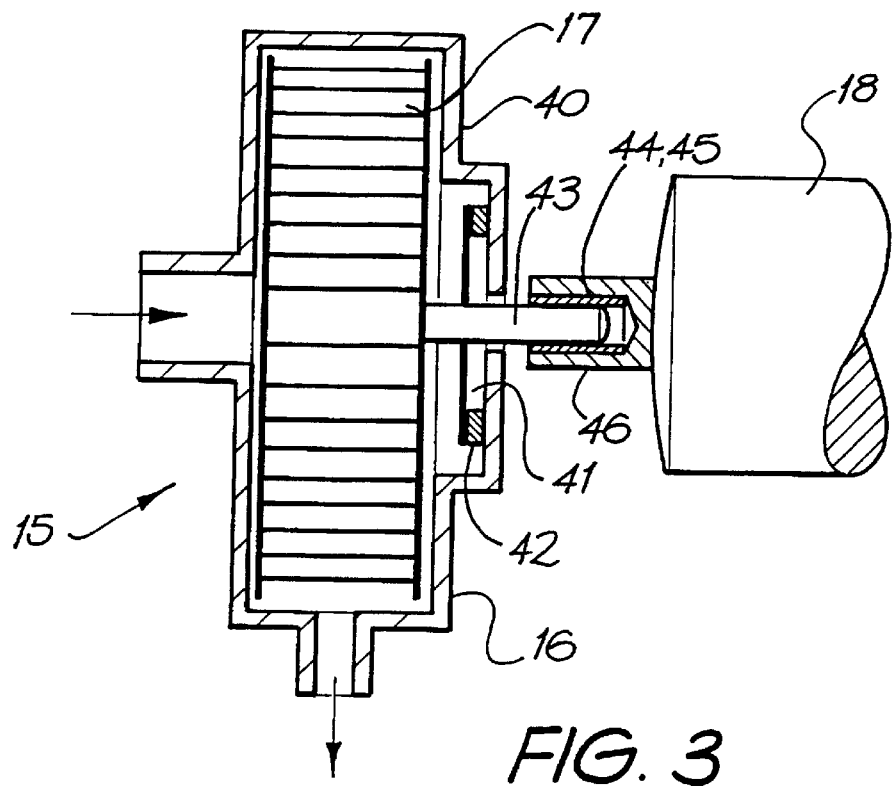
FIG. 3 shows one way of removably coupling a blower to an electric drive motor in the respiration assistors of FIGS. 1 and 2.

Although the various components of the respiration assistor have been illustrated in a schematic way, it will be understood that the gas circuit components will need to be constructed in a manner that permits cleaning and disinfection, as with normal anaesthetic circuit components. Similarly, the motor and other electrical components must be sealed effectively against high oxygen and nitrous oxide concentrations in the patient circuit. Conventional techniques may be employed to meet these requirements, but FIGS. 3 and 4 illustrate constructions that may be employed in the fabrication of the blower 15 and the electrically actuatable expiratory valve 23.

In the case of the blower 15, the rotor 17 is housed within a casing 40. The drive shaft 43 for the rotor passes through a membrane-type seal 41 which is held removably in position by magnetic retainers 42. The casing 40 is removably secured to the motor housing 18, and the drive shaft 43 is removably (i.e. slidably) secured in press-fitting engagement within the rotor shaft 46 of the motor 18. For this purpose the rotor shaft 46 has an axial bore 44 which is bushed with a resilient sleeve 45.

Figure 4:
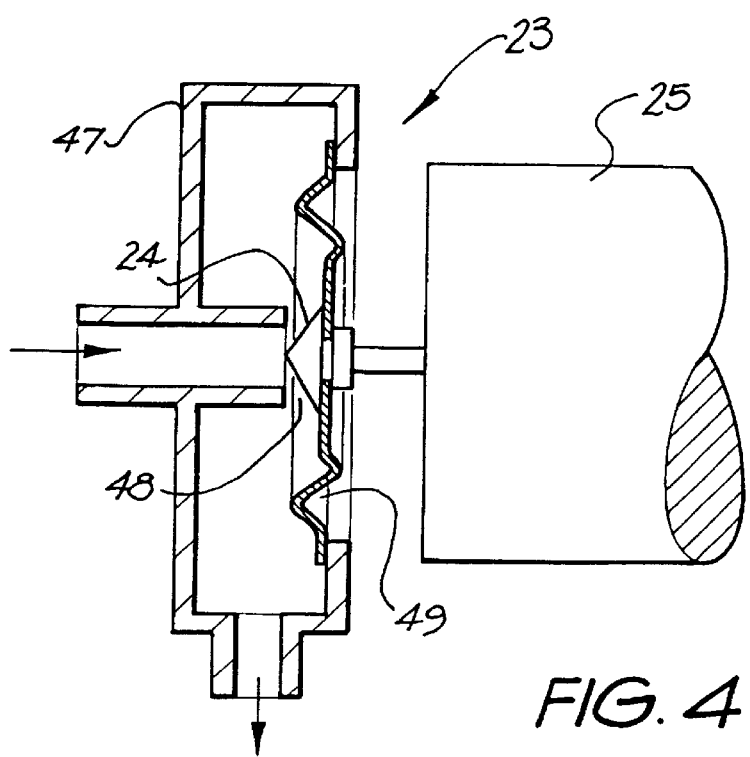
FIG. 4 shows one form of a solenoid operated expiratory valve for use in the respiration assistors as shown in FIGS. 1 and 2.

The solenoid actuatable valve 23 as shown in FIG. 4 has a casing 47 that includes an inlet port 48. A removable, resilient diaphragm is mounted to the casing 47 and carries the valve member 24. The diaphragm 49 and, hence, the valve member 24 are biased in a direction away from the inlet port 48 but are closed against the port with electrical energisation of the solenoid 25.

An audio and/or visual fault indicator 50 may be incorporated in the respiration assistor to provide indication of an alarm condition if gas is not detected to flow through the inspiratory side of the respiration assistor for a time interval that exceeds a predetermined period of time or if uninterrupted gas flow is detected. The absence of gas flow will indicate the cessation of patient breathing or circuit obstruction, and continuous gas flow will indicate a significant leak in the system. For this arrangement the control circuit and power supply 19 will incorporate an electronic timer and a driver stage for energising the fault indicator 50 when no gas flow is detected over a time-out period or when gas flow continues uninterrupted over the time-out period.

Also, the respiration assistor may be arranged to provide a quasi-ventilator operation in the event that patient breathing is detected to cease. For this function the timer within the control circuit/power supply 19 may be activated to effect cyclic excitation of the blower motor 18.

The embodiments of the invention as above described and illustrated offer the following features:

(a) With a patient breathing spontaneously the respiration assistor remains in-circle and does not affect the normal function of the circle absorber.

(b) The respiration assistor may be switched on at any time by an anaesthetist to provide in-phase respiratory assistance.

(c) No adjustment is required to be made in the setting of the APL valve.

(d) The reservoir bag is retained and may be used to monitor lung movement.

(e) Fault condition indication is provided.

What is claimed is:

1. A respiration assistor for use in an anesthesia breathing system for providing in-phase respiratory assistance to a spontaneously breathing patient and which comprises:
   a) a first gas supply passage,
   b) a first connecting means for connecting the first gas supply passage in circuit with a patient side of the breathing system and, hence, to a first gas supply of anesthetic gas,
   c) a gas flow detector located in the first gas supply passage and arranged to detect flow of the anesthetic gas induced by spontaneous inspiratory breathing by the patient,
   d) an electrically activatable pressure booster connected in circuit with the first gas supply passage and arranged when actuated to deliver the anesthetic gas to the patient under a pressure sufficient to assist the spontaneous inspiratory breathing of the patient whereby the end-expired $CO_2$ level of the patient is maintained at or near a normal physiological level, the pressure booster being blower that permits substantially free flow of the inspired anesthetic gas therethrough when the pressure booster is not activated whereby the spontaneously breathing patient draws the anesthetic gas through the pressure booster in the event that the respiration assistor malfunctions,
   e) a gas delivery conduit for delivering pressurized anesthetic gas to the patient from the pressure booster,
   f) an electrically actuatable expiratory valve,
   g) a gas exhaust conduit for carrying expired gas from the patient to the expiratory valve,
   h) a second connecting means for connecting a second gas supply in circuit with the first gas supply in circuit with the first gas supply passage, and
   i) an electrical control circuit arranged to:
      i. effect activation of the pressure booster and closure of the expiratory valve upon detection of inspired gas flow through the gas flow detector, and
      ii. effect deactivation of the pressure booster and opening of the expiratory valve in the absence of inspired gas flow through the gas flow detector.

2. The respiration assistor as claimed in claim 1 wherein the pressure booster further comprises a motor which drives the blower.

3. The respiration assistor as claimed in claim 2 wherein the pressure booster comprises a motor driven centrifugal blower having a vaned drum rotor through which inspired gas may be drawn by a patient.

4. The respiration assistor as claimed in claim 2 wherein the blower is removably coupled to the motor.

5. The respiration assistor as claimed in claim 3 wherein the rotor has a shaft that mates in sliding, press-fitting engagement within a bore of a drive shaft of the motor.

6. The respiration assistor as claimed in claim 2 wherein the control circuit is arranged to effect energization of the motor only when the blower is to be activated.

7. The respiration assistor as claimed in claim 2 wherein the control circuit is arranged to effect constant energization of the motor and to effect coupling of the blower to the motor when the blower is to be activated.

8. The respiration assistor as claimed in claim 3 wherein a drive shaft for the rotor passes through a membrane to couple with a rotor shaft of the motor, and wherein the membrane is removably secured within a casing of the centrifugal blower.

9. The respiration assistor as claimed in claim 2 wherein a gas flow activated inspiratory valve is located in the first gas supply passage.

10. The respiration assistor as claimed in claim 9 wherein the gas flow detector is integrated in the inspiratory valve.

11. The respiration assistor as claimed in claim 10 wherein the gas flow detector includes a photoelectric sensor which is arranged to provide an output signal that indicates the existence of inspired gas flow with opening of the inspiratory valve.

12. The respiration assistor as claimed in claim 2 wherein the electrically actuatable expiratory valve comprises a solenoid actuated valve member that normally is biased into an open condition but which is arranged to be actuated to a closed condition upon detection of inspired gas flow through the gas flow detector.

13. The respiration assistor as claimed in claim 12 wherein the electrically actuatable expiratory valve comprises a valve casing and wherein a valve member is carried by a diaphragm that is removably secured within the casing.

14. The respiration assistor as claimed in claim 2 wherein a fault indicator is electrically connected to the control circuit, and wherein the control circuit is arranged to generate and apply a fault condition signal to the fault indicator if gas is not detected to flow through the gas flow detector for a time interval that exceeds a predetermined time interval.

15. The respiration assistor as claimed in claim 14 wherein the control circuit is arranged also to generate and apply a fault condition signal to the fault indicator if an uninterrupted flow of gas is detected in the gas flow detector.

* * * * *